United States Patent [19]

Schaeffer

[11] Patent Number: 5,132,448
[45] Date of Patent: Jul. 21, 1992

[54] PREPARATION OF ALPHA-CHLORO PHOSPHORUS YLIDES

[75] Inventor: Bernd Schaeffer, Dierbach, Fed. Rep. of Germany

[73] Assignee: BASF Aktiengesellschaft, Ludwigshafen, Fed. Rep. of Germany

[21] Appl. No.: 580,857

[22] Filed: Sep. 11, 1990

[30] Foreign Application Priority Data

Sep. 30, 1989 [DE] Fed. Rep. of Germany ....... 3932748

[51] Int. Cl.$^5$ .................... C07B 39/00; C07C 255/10
[52] U.S. Cl. ...................... 558/385; 564/15; 568/13; 568/16
[58] Field of Search .................... 568/13, 16; 558/385; 564/15

[56] References Cited

PUBLICATIONS

Topics in Stereochemistry, vol. 5, Wiley-Interscience, Editors Eliel et al., Schlosser.
The Condensed Chemical Dictionary, Seventh Ed., Reinhold Publishing Corp.
Hackh's Chemical Dictionary, 1953, Third Edition.
Chambers Science and Technology Dictionary.
Topics in Phosphorus Chemistry vol. 5: P$^{31}$ Nuclear Magnetic Resonance, Crutchfield et al., Interscience Publishers.
Chem. Ber., 90 (1962) 3303, Märkl.
Bestmann et al., Synthesis, (1970) 590.
Denney et al., J. Org. Chem. 27 (1962) 998.

Primary Examiner—Joseph Paul Brust
Assistant Examiner—M. S. H. Gabilan
Attorney, Agent, or Firm—Keil & Weinkauf

[57] ABSTRACT

α-Chloro phosphorus ylides of the formula I

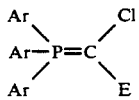

I where the Ar radicals are identical or different aryl groups, and E is a substituent which stabilizes the ylide (I), are prepared by reacting a phosphonium salt of the formula II

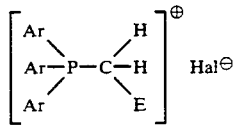

II where Hal is chlorine, bromine or iodine, with a chlorinating agent, using bleaching powder as chlorinating agent.

5 Claims, No Drawings

PREPARATION OF ALPHA-CHLORO PHOSPHORUS YLIDES

The present invention relates to a novel process for preparing α-chloro phosphorus ylides of the formula I

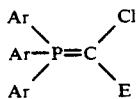

where the Ar radicals are identical or different aryl groups, and E is a substituent which stabilizes the ylide (I), by reacting a phosphonium salt of the formula II

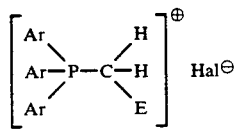

where Hal is chlorine, bromine or iodine, with a chlorinating agent.

It is known from the paper by Märkl (Chem. Ber., 95 (1962) 3003) that phosphonium salts of the type of formula II can be reacted with chlorine or, preferably, iodobenzene dichloride to give the corresponding chloro ylides I.

A similar process in which the chlorinating agent is N-chloro-4-toluenesulfonamide sodium salt (chloramine T) is described by Bestmann et al. (Synthesis, (1970) 590).

Denney et al. (J. Org. Chem. 27 (1962) 998) proposed carrying out the same reaction by chlorination with chlorine, preferably in the presence of a tertiary amine, and with tert-butyl hypochlorite, although the latter reagent is said to be less satisfactory.

Because these chlorinating agents are either relatively costly, give inadequate yields or, like gaseous chlorine, involve technical problems, it was an object of the present invention to provide a more straightforward and economic chlorination of II to give I.

We have found that this object is achieved by a process for preparing α-chloro phosphorus ylides of the formula I

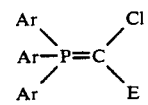

where the Ar radicals are identical or different aryl groups, and E is a substituent which stabilizes the ylide (I), by reacting a phosphonium salt of the formula II

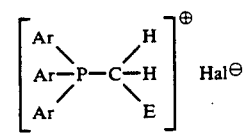

where Hal is chlorine, bromine or iodine, with a chlorinating agent, which comprises using bleaching powder as chlorinating agent.

The chlorination according to the invention can be applied in general to those starting compounds II in which E is a substituent which stabilizes the ylide (I), ie.

a group which is able to stabilize the partial negative charge on the carbon of the ylide (I) by delocalization over resonance structures (Manfred Schlosser, in "Topics in Stereochemistry", Ed. E.L. Eliel and N.L. Allinger, Wiley Interscience, (1970), Volume 5, page 1).

Radicals of this type are, in particular, the cyano group and all groups bonded via carbonyl, sulfonyl or aryl to the α atom of the phosphonium salt.

The following specific radicals are particularly preferred in this connection:

Carbamoyl groups

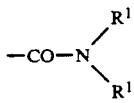

where the $R^1$ radicals are identical or different and are hydrogen, $C_1$–$C_6$–alkyl such as methyl or ethyl, $C_5$–$C_6$–cycloalkyl or aryl.

—CO–$R^2$ groups where $R^2$ is one of the $R^1$ radicals, hydroxyl, $C_1$–$C_6$–alkoxy such as ethoxy, or aryloxy, —SO$_2$–$R^2$ groups and phenyl.

Findings to date indicate that the process according to the invention does not depend on the nature of the aryl substituents (Ar) so that, in principle, ylides of any desired tertiary phosphines can be used.

Phenyl radicals which are unsubstituted or substituted up to 3 times by, in particular, fluorine, chlorine and bromine, and $C_1$–$C_{10}$–alkyl and $C_1$–$C_4$–alkoxy, are particularly preferred.

Examples of preferred starting compounds II are: acetylmethyltriphenylphosphonium chloride cyanomethyltriphenylphosphonium chloride methoxycarbonylmethyltriphenylphosphonium chloride ethoxycarbonylmethyltriphenylphosphonium chloride and ethoxysulfonylmethyltriphenylphosphonium chloride.

The phosphonium salts II are known or can be obtained in a conventional manner by quaternization of triarylphosphines PAr$_3$ with E-CH$_2$X where X is an anionic leaving group such as chlorine, bromine or iodine.

The bleaching powder which is to be used according to the invention as chlorinating agent is, as is known, a commercially available mixed salt of calcium with the approximate composition

3 Ca Cl (OCl)·Ca (OH)$_2$·5H$_2$O and is obtained from chlorine and calcium hydroxide. Essential for the chlorinating action are the hypochlorite ions which comprise the active chlorine content, which may, depending on the degree of chlorination of the calcium hydroxide, be less than indicated by the above formula.

The reaction is preferably carried out in the presence of a solvent in which the phosphonium salt II is at least partially, and the product I is completely, soluble.

Suitable solvents, which are used in amounts of about 0.3 to 2, preferably 0.5 to 1.5, liters per mole of II, are, in particular, halohydrocarbons such as dichloromethane or chloroform, ethers such as diethyl ether or tetrahydrofuran, esters such as ethyl acetate, aliphatic and aromatic hydrocarbons such as hexane, cyclohexane, benzene and toluene, and, particularly preferably, alcohols such as methanol and ethanol, and ketones such as acetone. The presence of small amounts of water does not interfere with the course of the reaction.

It is advisable to add the bleaching powder a little at a time to a solution of II. Because only 75 % of the hypochlorite, ie. the active chlorine, usually reacts when used in equimolar amounts, an acid, preferably hydrochloric acid, can be used to liberate the remainder as chlorine to complete the reaction.

The reaction temperature depends on the reactivity of the phosphonium salt but is generally from −10 to 120° C., usually from −10 to 60, preferably 0 to 30° C.

After the chlorination is complete, the organic phase is separated from the solids and, if an aqueous acid has been used, from the aqueous phase. The organic phase can be worked up in a conventional manner to give the products I or be used immediately for further reactions.

The phosphorus ylides I are, as is known, valuable intermediates for organic syntheses, especially for preparing α-chlorocinnamic acid derivatives with herbicidal activity, such as
ethyl 2,α-dichloro-5-(3,4,5,6-tetrahydrophthalimido) cinnamate or ethyl 2,α-dichloro-4-fluoro-5-(3,4,5,6-tetrahydrophthal-imido)cinnamate.

EXAMPLES 1 TO 3

Preparation of α-chloro phosphorus ylides
$Ph_3P=C(Cl)-E$

An amount of bleaching powder containing 75 mmol (Example 3: 50 mmol) of active chlorine was added a little at a time at from 20° to 25° C. to a solution of 50 mmol of a triphenylphosphonium chloride (II) [$Ph_3P-CH_2-E$]⊕Cl⊖ in 50 ml of ethanol within 45 min. 45 ml of aqueous ethanolic hydrochloric acid which contained 90 mmol of hydrogen chloride were then added to the reaction mixture, which was then stirred at from 20° to 25° C. for 1 h. Conventional working up provided the ylides I in the following yields:

| Example | E | Yield [%] |
|---|---|---|
| 1 | —COCH$_3$ | 100 |
| 2 | —CN | 74 |
| 3 | —CO$_2$CH$_2$CH$_3$ | 80 |

We claim:
1. A process for the preparing α-chloro phosphorus ylides of the formula (I)

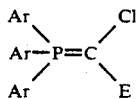

where the Ar radicals are identical or different aryl groups, and E is a substitutent selected from the group consisting of
cyano
carbamoyl (—CO—N(R$^1$)$_2$), where the R$^1$ radicals can be identical or different and are each hydrogen, C$_1$-C$_6$-alkyl, C$_5$-C$_6$-cycloalkyl or aryl
—CO—R$^2$ where R$^2$ is one of the R$^1$ radicals, hydroxyl, C$_1$-C$_6$-alkoxy or aryloxy
—SO—R$^2$ or
phenyl,
which stabilizes the ylide (I), which comprises reacting a phosphonium salt of the formula II

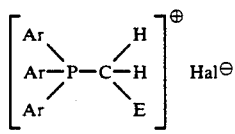

where Hal is chlorine, bromine or iodine, with bleaching powder as a chlorinating agent.

2. The process of claim 1, wherein the aryl groups in formula I are identical or different and are each phenyl unsubstituted or substituted with one to three radicals selected from the group consisting of fluorine, chlorine, bromine, C$_1$-C$_{10}$-alkyl, C$_1$-C$_4$-alkoxy and combinations thereof.

3. The process of claim 1, wherein the phosphonium salt (II) is selected from the group consisting of
acetylmethyltriphenylphosphonium chloride
cyanomethyltriphenylphosphonium chloride
methoxycarbonylmethyltriphenylphosphonium chloride
ethoxycarbonylmethyltriphenylphosphonium chloride and
ethoxysulfonylmethyltriphenylphosphonium chloride.

4. The process of claim 1, wherein the reaction is carried out in the presence of a solvent selected from the group consisting of halohydrocarbons, ethers, esters, aliphatic and aromatic hydrocarbons, alcohols and detones.

5. The process of claim 1, wherein the reaction is carried out at a temperature of −10° C. to +120° C.

* * * * *

UNITED STATES PATENT AND TRADEMARK OFFICE
CERTIFICATE OF CORRECTION

PATENT NO. : 5,132,448
DATED : July 21, 1992
INVENTOR(S) : Bernd SCHAEFER

It is certified that error appears in the above-identified patent and that said Letters Patent is hereby corrected as shown below:

Cover page, under Inventor: "Schaeffer" should read -- Schaefer --.

Claim 4, column 4, line 50: "detones" should read -- ketones --.

Signed and Sealed this

Tenth Day of August, 1993

Attest:

MICHAEL K. KIRK

Attesting Officer

Acting Commissioner of Patents and Trademarks